United States Patent

Boaz

[11] Patent Number: 5,126,268
[45] Date of Patent: Jun. 30, 1992

[54] ALCOHOL-ESTER SPARATION BY REACTION WITH ACETATE

[75] Inventor: Neil W. Boaz, Waterloo, N.Y.

[73] Assignee: Eastman Kodak Company, Rochester, N.Y.

[21] Appl. No.: 660,839

[22] Filed: Feb. 26, 1991

Related U.S. Application Data

[63] Continuation-in-part of Ser. No. 501,570, Mar. 30, 1990, abandoned.

[51] Int. Cl.⁵ .................. C12P 41/00; C07C 309/68; C07C 33/03
[52] U.S. Cl. ..................... 435/280; 558/51; 558/52; 568/857; 568/868; 435/130; 435/157; 435/158
[58] Field of Search .............. 435/280, 130, 157, 158; 558/51, 52; 568/857, 868

[56] References Cited

U.S. PATENT DOCUMENTS

| | | | |
|---|---|---|---|
| 4,732,853 | 3/1988 | Whitesides et al. | 435/280 |
| 4,865,771 | 9/1989 | Francalanci et al. | 562/567 |
| 4,921,798 | 5/1990 | Boaz | 435/146 |
| 4,923,810 | 5/1990 | Walts et al. | 435/117 |

FOREIGN PATENT DOCUMENTS 197484  10/1986  European Pat. Off. ............ 435/130

Primary Examiner—Carolyn Elmore
Attorney, Agent, or Firm—J. Jeffrey Hawley

[57] ABSTRACT

A process is disclosed for the isolation of an enantiomerically enriched alcohol from a first mixture of an enantiomerically enriched 1-arylsulfonate-2-hydroxy-3-butene and an enantiomerically enriched 1-arylsulfonate-2-acyloxy-3-butene. The process includes the steps of:

(a) contacting the mixture with a reagent capable of reacting with said 1-arylsulfonate-2-hydroxy-3-butene to remove the arylsulfonate group and produce a mixture of dihydroxybutene monoesters thereby forming a second mixture containing said dihydroxybutene monoesters and unreacted enantiomerically enriched 1-arylsulfonate-2-acyloxy-3-butene (b) contacting the second mixture with reagents capable of hydrolyzing all of the acyl groups in said mixture to hydroxy groups so as to produce a third mixture comprising 1,2-dihydroxy-3-butenes and enantiomerically enriched 1-arylsulfonate-2-hydroxy-3-butene;

(c) washing said third mixture with water so as to remove said 1,2-dihydroxy-3-butenes.

7 Claims, No Drawings

ALCOHOL-ESTER SPARATION BY REACTION WITH ACETATE

CROSS REFERENCE TO RELATED APPLICATIONS

The present invention is a continuation-in-part of U.S. Ser. No. 501,570 filed Mar. 30, 1990 entitled METHOD FOR THE PREPARATION OF OPTICALLY ACTIVE α, β-UNSATURATED EPOXIDES in the names of Boaz and Laumen. That parent application was abandoned as of the filing data accorded this application.

Reference is made to the following copending and commonly assigned applications, filed on even date herewith by Neil W. Boaz:

U.S. Ser. No. 660,830, entitled ALCOHOL-ESTER SEPARATION BY RECRYSTALLIZATION,

U.S. Ser. No. 660,837, entitled PROTECTED HYDROXY METHOD FOR ALCOHOL-ESTER SEPARATION, and U.S. Ser. No. 660,838, entitled ALCOHOL-ESTER SEPARATION BY REACTION WITH BICARBONATE IN POLYHYDROXY SOLVENT.

FIELD OF THE INVENTION

The present invention relates to a process for producing enantiomerically enriched compounds from a mixture which can be derived from the enzymatic enantioselective hydrolysis of a racemic ester or the enzymatic enantioselective esterification of a racemic alcohol. The resulting enantiomerically enriched compounds find a number of uses as starting materials for other compounds. Some of the compounds are useful, for example, for the production of 2-deoxy-D-ribose. Other compounds are useful in the preparation of leukotrienes.

BACKGROUND OF THE INVENTION

Chemoenzymatic synthesis is a preparative strategy which employs both chemical and biocatalytic steps in a reaction sequence. The biocatalytic transformations convert one organic compound to another by the use of enzymes, either isolated or as part of biological systems. These biocatalysts (enzymes) are in principle the same as any other type of catalyst. However, there are circumstances where these biocatalysts are especially useful, such as the induction of chirality due to enzyme enantiospecificity. These enzymatic reactions occur under mild conditions and are often more environmentally acceptable than classical chemical processes.

Lipases are the closest to optimum biocatalysts. They are isolated extracellular enzymes whose natural function is to hydrolyze glycerol esters. Many have wide substrate acceptability for ester hydrolysis, or, under the correct conditions, alcohol esterification. They are readily (and often cheaply) available and are experimentally simple, requiring no added cofactors and affording no side products. Not surprisingly these enzymes have been the most thoroughly studied for biocatalytic use in organic chemistry.

There are two types of substrate classes for lipase-catalyzed reactions. Meso or prochiral substrates constitute the first and most widely-studied class. The inherent chirality of the lipase distinguishes between two prochiral functions (esters or alcohols) on the same molecule to afford 100% conversion to (optimally) a single enantiomer.

The second class of substrates are the racemic systems, in which (optimally) only one of two enantiomers is recognized and hydrolyzed (or esterified) by the lipase, affording a 50% conversion to product and 50% recovered starting material of opposite configurations. This mixture must be physically separated to complete the enantiomeric differentiation. For substrates in which the acid rather than the alcohol portion is of interest, the separation is often possible by simple aqueous base extraction.

Alcohol-based substrates pose the most challenging separation problems due to the gross physical similarity between the alcohol and ester. It is to separations of this type that the present invention is directed.

Chemoenzymatic synthesis of optically active epoxybutadiene (hereinafter EpB) is a potentially attractive preparative method since a readily available source of EpB has recently become available. Novel, simple, and efficient preparations of optically pure C4 synthons derived from EpB would be synthetically useful, since most currently available chiral synthons have a three- or five-carbon backbone due to availability from natural sources. In fact, chain elongation of C3 synthons from the chiral pool currently comprises the major method for the preparation of optically active EpB and the corresponding diol (1,2-dihydroxy-3-butene).

For example, an early route to S-1,2-dihydroxy-3-butene and S-EpB relied on C6 D-mannitol (two identical three-carbon pieces) as the chiral starting material. (Baer, E.; Fischer, H. O. L. J. Biol. Chem. 1939, 128, 463) After formation of the terminal (symmetrical) diacetonide, the vicinal diol was oxidatively cleaved with lead tetraacetate to provide two molecules of the unstable acetonide of the three-carbon synthon R-glyceraldehyde. Wittig reaction with methylene triphenylphosphorane afforded 1,2-dihydroxybutene acetonide which was readily deprotected to the optically active 1,2-dihydroxybutene. Monotosylation of the diol and base treatment afforded optically active EpB. (Crawford, R. J.; Lutener, S. B.; Cockcroft, R. D. Can. J. Chem. 1976, 54, 3364.)

The corresponding R enantiomers were available from the antipodal three carbon synthon S-glyceraldehyde acetonide which has been prepared from L-ascorbic acid by several routes. After initial differential protection of the hydroxyl groups by sequential actonide formation and methylation, ozonolysis and lithium aluminum hydride treatment afforded S,S-1,2,3,4-tetrahydroxybutane 1,2-acetonide. Lead tetraacetate oxidative cleavage resulted in the desired S-glyceraldehyde acetonide. This material can be transformed to optically active R-1,2-dihydroxy-3-butene and ultimately to R-EpB.

Alternatively, optically active 1,2-dihydroxy-3-butene can be prepared from one of the few four carbon synthons available from the chiral pool, tartaric acid. After preparation of the acetonide and reduction of the carboxyl groups, formic acid-induced rearrangement and hydrolysis of the resulting formates afforded the desired diol. This can be transformed to optically active EpB.

All routes suffer from synthetic problems. The oxidation steps mentioned above can be troublesome and produce highly toxic (lead) by-products. The first two routes also involve a cumbersome Wittig olefination of glyceraldehyde acetonide, itself a rather unstable species. In addition, each of the two routes can only be utilized for a single (but complementary) enantiomer due to the commercial availability of only D-mannitol and L-ascorbic acid. The route from tartaric acid is complicated by the formation of 1,4-dihydroxy-2-butene during the rearrangement reaction. Separation of this isomer from the desired 1,2-dihydroxy-3-butene is not trivial.

In actuality, only the route from tartaric acid is directed towards C4 synthons. The other schemes afford C4 materials as an afterthought by chain extension. A more direct approach, the synthesis of optically active C4 synthons from corresponding racemic C4 starting materials, would afford greater versatility for the preparation of diverse organic molecules. Therefore, the preparation of optically active EpB and derivatives (from racemic EpB) using biocatalysis technology is of great interest. An enantioselective lipase-catalyzed hydrolytic approach to this problem seemed promising due to the presence of diverse oxygen functionalities in many EpB derivatives.

EpB can be converted to a racemic ester by a number of routes. This ester is then subjected to enzymatic enantioselective hydrolysis to produce a mixture of enantiomerically enriched alcohol and enantiomerically enriched ester. While these compounds can be separated using chromatographic separation techniques, this is not practical on a large scale. Unfortunately, as mentioned previously, the separation of the alcohol from the ester is difficult because of the similarity of the physical characteristics of these compounds.

Thus, the present invention is directed to the problem of separating an optically active alcohol from a related optically active ester.

SUMMARY OF THE INVENTION

In accordance with the present invention, there is provided a process for the isolation of an enantiomerically enriched alcohol from a first mixture of an enantiomerically enriched 1-arylsulfonate-2-hydroxy-3-butene and an enantiomerically enriched 1-arylsulfonate-2-acyloxy-3-butene, the process comprising the steps of:

(a) contacting the mixture with a reagent capable of reacting with said 1-arylsulfonate-2-hydroxy-3-butene to remove the arylsulfonate group and produce a mixture of dihydroxybutene monoesters thereby forming a second mixture containing said dihydroxybutene monoesters and unreacted enantiomerically enriched 1-arylsulfonate-2-acyloxy-3-butene (b) contacting the second mixture with reagents capable of hydrolyzing all of the acyl groups in said mixture to hydroxy groups so as to produce a third mixture comprising 1,2-dihydroxy-3-butenes and enantiomerically enriched 1-arylsulfonate-2-hydroxy-3-butene;

(c) washing said third mixture with water so as to remove said 1,2-dihydroxy-3-butenes.

The invention is particularly useful in separating the alcohol and ester that are formed by the enzymatic enantioselective hydrolysis of a racemic acetate or the enzymatic enantioselective esterification of a racemic alcohol, with the racemic acetate or alcohol each in turn formed from 3,4-epoxy-1-butene. Thus, the invention is particularly useful for the isolation of an enantiomerically enriched 1-arylsulfonate-2-hydroxy-3-butene from a mixture containing a 1-arylsulfonate-2-hydroxy-3-butene and a 1-arylsulfonate-2-acyloxy-3-butene, with the isolated product derived from 1-arylsulfonate-2-acyloxy-3-butene.

DETAILED DESCRIPTION OF THE INVENTION

In preferred embodiments, the mixture is represented by:

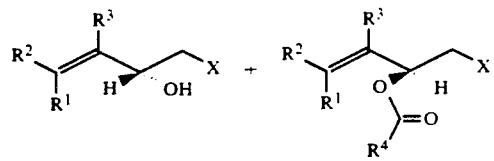

wherein each R is a group stable to nucleophilic, basic, and mildly acidic conditions and is independently selected from H, straight- or branched-chain substituted or unsubstituted alkyl, aryl, substituted aryl, arylalkyl, non-nitrogen-containing heteroaryl or substituted heteroaryl, or halogen. Substituents as designated above can be chosen from halogen, alkoxy, aryloxy, cyano, arylthio, alkylthio.

X is selected from halogen (F, Cl, Br, I) or sulfonate esters such as p-toluenesulfonate, phenylsulfonate, p-bromobenzenesulfonate, 4-chloro-3-nitrobenzenesulfonate, 2,5-dichlorobenzenesulfonate, 5-dimethylamino-1-naphthalenesulfonate, 2,4-dinitrobenzenesulfonate, p-iodobenzenesulfonate, 1-naphthalenesulfonate, 2-naphthalenesulfonate, o-nitrobenzenesulfonate, m-nitrobenzenesulfonate, p-nitrobenzenesulfonate, 2-thiophenesulfonate, methanesulfonate, trifluoromethanesulfonate, and the like.

In the first step of the process of the invention, the mixture is reacted with reagents capable of reacting with the 1-arylsulfonate-2-hydroxy-3-butene to remove the arylsulfonate group and produce a mixture of dihydroxybutene monoesters. In preferred embodiments, the mixture is reacted with a reagent of the formula M+ OCOR'− wherein R' is selected from H, straight- or branched-chain substituted or unsubstituted alkyl, aryl, substituted aryl, arylalkyl, non-nitrogen-containing heteroaryl or substituted heteroaryl, and M = Na, K, Cs, R'4N (where R' is as defined above). The reaction can be conducted in a dialkyl ketone or a lower alcohol solvent at a temperature such that the alcohol component of the mixture reacts while the ester compound does not. This is most preferably at or below room temperature.

In the second step of the process, the mixture containing the dihydroxybutene monoesters and unreacted enantiomerically enriched 1-arylsulfonate-2-acyloxy-3-butene is reacted with reagents that are capable of hydrolyzing all of the acyl groups, including the acyl group in the 1-arylsulfonate-2-acyloxy-3-butene, to hydroxy groups. Mild acidic conditions are usually sufficient.

After the acyl groups have been removed, the resultant mixture contains dihydroxy compounds derived from the alcohol in the original mixture and the desired enantiomerically enriched hydroxy-tosylate derived from the ester in the original mixture. The dihydroxy compounds are easily removed from the hydroxy-tosylate by a water wash.

The resulting hydroxy-tosylate can be purified by crystallization to substantial optical purity.

It will be noted that the alcohol that is produced by this method is of the opposite optical configuration from the starting alcohol since it is derived from the starting ester. Thus, for example, if the starting mixture includes an R-alcohol and an S-ester, an S-alcohol will result.

Thus, the process of the invention can be illustrated, in its preferred embodiment, by the following reaction scheme:

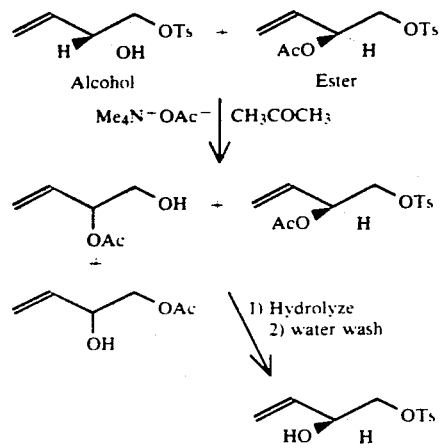

The invention relates to a method for the separation of an optically active alcohol from an optically active ester The preparation of a typical mixture of this type will be discussed. In this process, EpB is first converted to a racemic acetate. This acetate is then subjected to enzymatic hydrolysis to produce the desired starting mixture. It will be understood, however, that the method of obtaining the desired mixture as well as the particular mixture itself is not critical to the invention in its broadest aspect. The described route is merely a preferred route.

A useful racemic ester starting substrate for enzymatic hydrolysis can be prepared from EpB by two routes. For efficiency, a tosylate group was chosen as the 1-alkoxy substituent to allow ready displacement to form the dihydroxybutene monoesters. In addition, enzymatic hydrolysis of tosylated glycerol derivatives has been reported. (Hamaguchi, S.; Ohashi, T.; Watanabe, K. Agric. Biol. Chem. 1986, 50, 1629.) Groups other than tosylate can be used when other considerations become more important.

The 1-tosyloxy-2-acetoxy-3-butene substrate is also preferred since it can be hydrolyzed with high R-enantioselectivity by common lipases.

The racemic acetate substrate was prepared by one of two methods. The diol route began with racemic 1,2-dihydroxy-3-butene which could be prepared by reacting EpB with water under neutral conditions or with acid catalysis. The diol was treated with p-toluenesulfonyl chloride (p-TsCl) in pyridine at 4° C. to afford the desired monotosylate contaminated with about 10% of the corresponding ditosylate. The monotosylate could be selectively crystallized to afford pure monotosylate in 61% yield. Hydroxytosylate was acetylated under normal conditions (Ac2O, Et3N, CH2Cl2) to provide the acetoxy-tosylate (the desired racemic acetate) in 93% yield. The diol route is illustrated as follows:

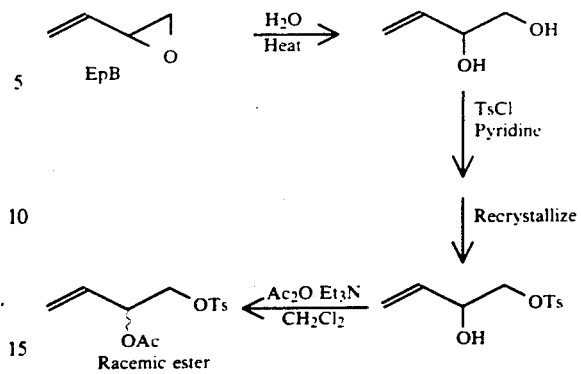

Alternatively, the acetoxy-tosylate could be prepared by initial reaction of EpB with acetic acid under palladium(0) catalysis to afford 1-hydroxy-2-acetoxy-3-butene. Tosylation under normal conditions (p-TsCl, Et3N, CH2Cl2, 88%) afforded the desired product. However, the isomeric inconsistency of the monoacetate material (acetyl migration during distillative purification) and the inseparability of the positional isomers of two intermediates posed significant problems, since the unwanted isomers complicated the enzymatic hydrolysis. Therefore, the former (diol) preparation is preferred.

In the next step, the racemic ester was hydrolyzed in the presence of a lipase. (Convenient lipases are Lipase SAM-II ® derived from *Pseudomonas fluorescens* and Lipase PS-30 ® derived from *Pseudomonas capacia*, both commercially available from Amano International Enzyme Company.)

The enzymatic enantioselective hydrolysis of the racemic ester proceeds using only a small amount (e.g., 50 mg crude lipase/0.1 mol racemic ester) of the lipase from *Pseudomonas fluoescens* or from *Pseudomonas capacia*. The reaction can be performed as an emulsion in aqueous pH 7 phosphate buffer under automatic titration conditions ("pH Stat", end point pH 7.00), allowing the reaction to be followed by the uptake of 1.000N NaOH. The reaction can be stopped at about 50% conversion, affording the R-enantiomer of the optically active alcohol and unreacted S-ester. The R-selectivity of the hydrolysis is very high, affording both enantiomers in high optical purity [both >80% enantiomeric excess (ee)] with an R to S hydrolysis rate ratio (E value) of between 200 and 300. This is what is meant by "enantiomerically enriched". (The E value is determined in accordance with the methods described in (a) Chen, C. S.; Fujimoto, Y.; Girdaukas, G.; Sih, C. J. *J. Am. Chem. Soc.* 1982, 104, 7294. or (b) Chen, C. S.; Wu, S. H.; Girdaukas, G.; Sih, C. J. *J. Am. Chem. Soc.* 1987, 109, 2812.) In the same manner, "substantially optically pure" means >98% ee.

Alternatively, the lipase isolated from *Pseudomonas Novo* sp. ATCC 21808 can be used, affording the same configurational selectivity with an E value of upwards of 300.

A solution or well-dispersed emulsion is important for the success of an enzymatic hydrolysis reaction. In certain instances the mixture of optically active alcohol and optically active ester formed an undesirable gel prior to completion of the hydrolysis, halting the reaction early. A 9:1 pH 7 Buffer:tetrahydrofuran solvent mixture avoided this problem and also afforded a more rapid hydrolysis reaction (rate increased by a factor of 2) without sacrificing enantioselectivity (E values of up to 254 were observed). The enzymatic hydrolysis is illustrated as follows:

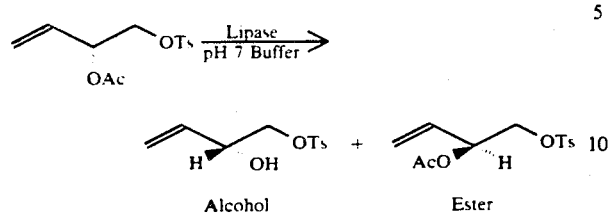

Substrate Preparation and Enzymatic Hydrolysis

Diol Preparation

Addition of Water to EpB

EpB (250g) was added to 800 mL of water, followed by 10 g of an acid resin. The reaction mixture was stirred at room temperature overnight. The catalyst was removed by filtration and the filtrate was concentrated at reduced pressure. Distillation of the residue 60°-65° C./1 mm) provided 3.4-dihydroxy-but-1-ene in 85% yield. $^1$H NMR (CDCl3): 5.9 (m, 1H); 5.4-5.2 (m, 2H); 4.25 (m 1H); 3.7 (m, 1H); 3.5 (m, 1H); 2.3 (br s, 1H). Ir(CCl4): 3600, 3499 (broad), 2900, 2880 cm$^{-1}$. Ms: 87, 70, 57, 42, 31, 29 m/e.

1-Tosyloxy-2-hydroxy-3-butene (Racemic Ester, diol route)

1,2-Dihydroxy-3-butene (20.00 g; 0.227 mol; 1.05 equiv) was dissolved in pyridine (200 mL). The reaction mixture was cooled in an ice bath and p-toluenesulfonyl chloride (p-TsCl) (41.11 g; 0.216 mol) was added in four portions over 30 min. After thorough mixing, the reaction mixture was placed at 4° C. for 18 h, at which time thin layer chromotography (hereinafter TLC) analysis indicated no p-TsCl. The mixture was concentrated to about half the original volume at reduced pressure from a 40° C. water bath and then diluted with ether (200 mL). The mixture was washed with water (100 mL), ice-cold 3N HCl until the washes remained acidic (2×100 mL), and saturated sodium bicarbonate (100 mL). After drying the organic solution (MgSO4), the solvent was removed to afford 41.73 g of a 91:9 mixture (1H nmr analysis) of the desired compound and the corresponding di-tosylate. The crude product solidified over several days at −20° C. It was recrystallized from methylene chloride (50 mL) by the addition of hexanes (100 mL) and chilling to −20° C. to afford two crops (total 33.33 g; 61%) of the desired compound which was pure by TLC analysis, mp 38°-44° C. $^1$H nmr (300 MHz, CDCl3): 7.800 (2H, d, J=8.25 Hz); 7.356 (2H, d, J=8.19 Hz); 5.751 (1H, ddd, J=5.38, 10.46, 16.55 Hz); 5.378 (1H, br d, J=17.05 Hz); 5.247 (1H, br d, J=10.48 Hz); 4.396 (1H, m); 4.066 (1H, dd, J=3.39, 10.20 Hz); 3.906 (1H, dd, J=7.41, 10.22 Hz); 2.451 (3H, s); 2.276 (1H, d, J=4.50 Hz). IR (KBr, cm$^{-1}$): 3520 (s,b); 1650 (w); 1600 (s); 1350 (s); 1170 (s). Combustion Analysis: Theor—C, 54.53; H,5.82;N, 0. Found—C, 54.84; H, 5.86;N, <0.3.

1-Tosyloxy-2-acetoxy-3-butene

Tosylate from above (25.00 g; 0.103 mol) was dissolved in methylene chloride (125 mL) and cooled to 0° C. Triethylamine (21.5 mL; 0.155 mol; 1.5 equiv) was added followed dropwise by acetic anhydride (11.7 mL; 0.124 mol; 1.2 equiv). The reaction mixture was allowed to warm to room temperature and after 2.5 days no starting tosylate was visible by TLC analysis. The mixture was poured into ether (250 mL), washed with water (2×50 mL) and saturated sodium bicarbonate (50 mL), dried (MgSO4), and concentrated. The crude product was stirred with pH 7 phosphate buffer (100 mL) for 1.5 h to hydrolyze any excess acetic anhydride and extracted with ether (3×50 mL). The combined ether extracts were dried (MgSO4) and concentrated to afford 27.51 g (93%) of acetate product. $^1$H nmr (300 MHz, CDCl3): 7.786 (2H, d,J=8.26 Hz); 7.355 (2H, d, J=8.03 Hz); 5.710 (1H, ddd, J=6.23, 10.54, 17.05 Hz); 5.396 (1H, m); 5.324 (1H, d, J=16.72 Hz); 5.279 (1H, d, J=10.63 Hz); 4.09 (2H, m); 2.453 (3H, s); 2.017 (3H, s). IR (neat film, cm$^{-1}$): 1740 (s); 1645 (w); 1600 (m); 1360 (s); 1175 (s).

Optically active R-(+)-alcohol ([α]$D^{20}$+7.14°(c. 1.036, methanol)) afforded R-(+)-ester, [α]$D^{20}$+5.30° (c. 1.246, methanol), by this methodology.

Enzymatic Enantioselective Hydrolysis of Racemic Ester using SAM-II

Racemic ester described above (25.76 g; 90.6 mmol) and pH 7 phosphate buffer (90 g) were combined and vigorously stirred under pH Stat conditions (automatic titration—pH 7.00 end point). Once the pH had stabilized at 7.00, the lipase from Pseudomonas fluorescens (SAM II) (50 mg) was added. The mixture was stirred for 15 h under pH Stat conditions at which time 45.54 mL of 1.000N NaOH had been consumed. The mixture was extracted with methylene chloride (3x100 mL), dried (Na2SO4), and concentrated to afford 23.47 g (98% material recovery) of the mixture of alcohol and ester. A portion (about 350 mg) was flash chromatographed (elution with 1:2 ethyl acetate:hexanes) to afford R-alcohol (148 mg; 92% ee) and S-ester (195 mg; 94% ee). Enantiomeric excess was determined using a method analogous to that described in Dale et al, J. Org. Chem., 1969, Vol 33, p2543.

R-alcohol: [α]$D^{20}$+7.14° (c. 1.036, methanol)
S-ester: [α]$D^{20}$−5.29°(c. 1.324 methanol).

All other properties are as described above for the alcohol and the ester.

Enzymatic Enantioselective Hydrolysis of Racemic Ester using the lipase from Pseudomonas Novo Sp. ATCC 21808

Racemic ester prepared as above (1.42 g; 5.00 mmol) and pH 7 phosphate buffer (20 g) were combined and vigorously stirred under pH Stat (automatic titration—pH 7.00 end point) conditions. Once the pH had stabilized at 7.00, an ammonium sulfate suspension of the lipase from Pseudomonas novo Sp. ATCC 21808 (1.00 mL) was added. The mixture was stirred for 4 h under pH Stat conditions at which time 2.471 mL of 1.000N NaOH had been consumed (49.4 % conversion). The mixture was extracted with methylene chloride (3×20 mL), dried (MgSO4), and concentrated. The crude product was flash chromatographed using 3:1 hexanes:ethyl acetate as eluent to afford 670 mg (47%; 92% ee) of S-ester and 447 mg (37%; 98% ee) of R-alcohol (one overlap fraction). Enantiomeric excess was determined using a method analogous to that described in Dale et al, J. Org. Chem., 1969, Vol 33, p2543.

R-alcohol: [α]$D^{20}$+7.14° (c. 1.036, methanol)
S-ester: [α]$D^{20}$−5.29° (c. 1.324, methanol).

All properties of the alcohol and the ester are as reported above.

Reduction of the olefin of the R-alcohol afforded the corresponding (−)-1,2-butanediol monotosylate. This compound is known to possess the R-(−) configuration (Hamaguchi, et al. Agri. Biol. Chem. vol 50, pg 1629 (1986).

The following example is submitted for a further understanding of the invention:

EXAMPLE 1

Selective Reaction of R-alcohol with Tetramethylammonium Acetate in the presence of S-1-Tosyloxy-2-acetoxy-3-butene An approximately 1:1 mixture of R-alcohol and S-ester (10.05 g; 19.08 mmol each) was dissolved in acetone (50 mL). Tetramethylammonium acetate (3.81 g; 28.6 mmol; 1.5 equiv based on alcohol) was added and the reaction mixture was stirred overnight at room temperature. Thin layer chromotography (tlc) analysis indicated residual alcohol so additional Me4N+OAc− (1.27 g; 9.54 mmol; 0.5 equiv) was introduced. After stirring overnight at room temperature, a small amount of alcohol remained according to tlc analysis. Me4N-+OAc− (1.27 g; 9.54 mmol; 0.54 equiv) was again added, and after 6 additional hours at room temperature the alcohol was completely consumed as determined by tlc analysis. The reaction mixture was diluted with ether (100 mL), washed with water (3×50 mL), dried (MgSO4), and concentrated to afford 5.53 g of S-ester contaminated with butenediol monoacetates. All properties of S-ester are as reported previously.

S-1-Tosyloxy-2-hydroxy-3-butene

Crude S-ester (5.53 g; 19.08 mmol max.) from the tetramethylammonium acetate reaction above was dissolved in methanol (50 mL). Concentrated HCl (about 12N ; 0.5 mL) was added and the reaction mixture was stirred overnight at room temperature. Tlc analysis indicated residual ester, so more conc. HCl (0.5 mL) was added and the reaction mixture was stirred an additional day at room temperature to completely consume the esters. The reaction mixture was diluted with ether (100 mL), washed with saturated sodium bicarbonate (3×25 mL), dried (MgSO4), and concentrated to afford 3.58 g (39% from racemic esters) of S-alcohol which possessed 92% optical purity. (Enantiomeric excess was determined using a method analogous to that described in Dale et al, J. Org. Chem., 1969, Vol 33, p2543.) This indicated minimal racemization during the reaction sequence.

The crude product was recrystallized from ether (15 mL) by hexanes addition (30 mL) to afford 2.784 g (29% yield from racemic esters) of the S-alcohol, >98% ee. All properties of S-alcohol are as described above.

The present invention has been described with reference to particularly preferred embodiments thereof. However, it will be understood that modifications and extensions can be effected within the spirit and scope of the invention.

We claim:

1. A process for the isolation of an enantiomerically enriched alcohol from a first mixture of an enantiomerically enriched 1-arylsulfonate-2-hydroxy-3-butene and an enantiomerically enriched 1-arylsulfonate-2-acyloxy-3-butene, the process comprising the steps of:

(a) contacting the mixture with a lower alkonic acid salt reagent capable of reacting with said 1-arylsulfonate-2-hydroxy-3-butene to remove the arylsulfonate group and produce a mixture of dihydroxybutene monoesters thereby forming a second mixture containing said dihydroxybutene monoesters and unreacted enantiomerically enriched 1-arylsulfonate-2-acyloxy-3-butene (b) contacting the second mixture with reagents capable of hydrolyzing all of the acyl groups in said mixture to hydroxy groups so as to produce a third mixture comprising 1,2-dihydroxy-3-butenes and enantiomerically enriched 1-arylsulfonate-2-hydroxy-3-butene;

(c) washing said third mixture with water so as to remove said 1-2-dihydroxy-3-butene.

2. The process according to claim 1 wherein said reagent capable of reacting with said 1-arylsulfonate-2-hydroxy-3-butene to remove the arylsulfonate group and produce a mixture of dihydroxubutene monoesters is a reagent of the formula M+OCOR′− where R′ is selected from H, straight- or branched-chain substituted or unsubstituted alkyl, aryl, substituted aryl, arylalkyl, non-nitrogen-containing heteroaryl or substituted heteroaryl; and M=Na, K, Cs, R′4N where R′ is as defined above.

3. The process according to claim 1 wherein said first mixture is represented by the structures:

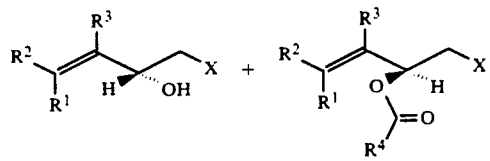

wherein

R¹, R² and R³ are independently selected from H, straight- or branched-chain substituted or unsubstituted alkyl, aryl, substituted aryl, arylalkyl, non-nitrogen-containing heteroaryl or substituted heteroaryl, or halogen;

R⁴ is selected from H, straight- or branched chain substituted or unsubstituted alkyl, aryl, substituted aryl, arylalkyl, non-nitrogen containing heteroaryl or substituted heteroaryl;

X is an aryl sulfonate ester.

4. The process according to claim 3 wherein said sulfonate esters are selected from the group consisting of p-toluenesulfonate, phenylsulfonate, p-bromobenzenesulfonate, 4-chloro-3-nitrobenzenesulfonate, 2,5-dichlorobenzenesulfonate, 5-dimethylamino-1-naphthalenesulfonate, 2,4-dinitrobenzenesulfonate, p-iodobenzenesulfonate, 1-naphthalenesulfonate, 2-naphthalenesulfonate, o-nitrobenzenesulfonate, m-nitrobenzenesulfonate, p-nitrobenzenesulfonate, 2-thiophenesulfonate, methanesulfonate and trifluoromethanesulfonate.

5. A process according to claim 1 wherein said first mixture is produced by the enzymatic enantioselective hydrolysis of a racemic ester.

6. The process according to claim 5 wherein said racemic ester is derived from epoxybutadiene.

7. A process according to claim 1 wherein said first mixture is a mixture of 1-tosyloxy-2-hydroxy-3-butene and 1-tosyloxy-2-acetoxy-3-butene.

* * * * *